United States Patent [19]

Blancke

[11] 4,243,044
[45] Jan. 6, 1981

[54] COUPLING CIRCUIT WITH DRIVEN GUARD

[75] Inventor: Timothy B. Blancke, Concord, Mass.

[73] Assignee: Hewlett-Packard Company, Palo Alto, Calif.

[21] Appl. No.: 940,403

[22] Filed: Sep. 7, 1978

[51] Int. Cl.³ ............................................. A61B 5/04
[52] U.S. Cl. .................................... 128/696; 128/902
[58] Field of Search ............... 128/695, 696, 901, 902, 128/639–643, 700, 702, 703, 704, 705, 706, 708, 709, 710, 908

[56] References Cited

U.S. PATENT DOCUMENTS

| | | | |
|---|---|---|---|
| 3,521,087 | 7/1970 | Lombardi | 128/908 |
| 3,699,389 | 10/1972 | Holsingel | 128/908 |
| 3,757,778 | 9/1973 | Braham | 128/696 |
| 3,868,948 | 3/1975 | Graetz | 128/209 |
| 3,880,146 | 4/1975 | Everett | 128/710 |

Primary Examiner—William E. Kamm
Attorney, Agent, or Firm—Donald N. Timbie

[57] ABSTRACT

In signal measurement circuits which are referred to a floating ground and which derive their input signals from electrodes attached to a patient's body, the effects of common mode potentials on the patient's body are minimized without requiring any patient electrodes other than those acting as signal sources, by using a unity gain amplifier to drive the floating ground toward the common mode potential on the patient's body.

This process is accomplished without significantly degrading the isolation impedance between the measurement circuits and true ground.

The patient is protected from hazardous electrical shock by incorporating current limiting devices in the unity gain amplifier.

6 Claims, 3 Drawing Figures

COUPLING CIRCUIT WITH DRIVEN GUARD

BACKGROUND OF THE INVENTION

In monitoring the condition of a patient's heart, potentials produced by heart action at different points on the body are picked up by electrodes applied to these points and the differences between the potentials are coupled to the monitoring apparatus that is referenced to true ground via suitable circuits. In order to protect the patient from the possibility of electrical shock, any path between the patient and true ground must have a very high impedance. Accordingly, any circuit that is directly coupled to the patient is referenced to a floating ground called a "guard". Unfortunately, however, the patient is generally within one or more ambient electrical fields from such sources as lights or power cords that produce what is known as a "common mode voltage", $V_{CM}$, on his body. The impedance looking back from each electrode to the patient's body and the impedance looking forward from each electrode to the floating ground form a conventional four-element bridge circuit which is excited by some fraction of the $V_{CM}$. If the bridge happens to be in balance, the $V_{CM}$ introduces no problem, but this is seldom if ever the case because the impedance between each electrode and the patient's body can vary over wide limits. Any imbalance causes a portion of the common mode potential $V_{CM}$ to add to or subtract from the difference between the potentials at the points of interest on the body so as to cause errors in the signal derived therefrom.

A solution to this problem that has been used for a long time is to apply a reference electrode to the patient's body and connect it to the floating ground or guard in such manner as to make the patient have nearly the same potential as the guard, thereby reducing the effect of the common mode voltage on the floating circuit.

Whereas this scheme works well, the reference electrode is a source of error if it is not properly applied, so that as much care and time must be taken in applying it to the patient's body as in applying the other electrodes. Furthermore, because it provides no useful physiological information it may be a source of confusion to a user.

BRIEF DISCUSSION OF THE INVENTION

This invention eliminates the need for a reference electrode without in any way impairing the safety of the patient. At the same time, excellent rejection of the effects of common mode potentials is attained. The circuits connected to the patient are referred to floating ground or guard as before, but instead of driving the potential of the patient toward the common mode potential of the guard, as has been done, the guard is driven toward the common mode potential of the patient. This is accomplished by applying the common mode potential on the floating circuits to control means for causing current to flow from true ground through the stray impedance between guard and true ground. If the current has the correct value and direction, the guard will have the same common mode potential as the floating circuits. Under such conditions, the bridge is not excited by the common mode potential and no addition to or subtraction from the desired signal voltages occurs.

Inasmuch as the control means includes connections to true ground, the safety of the patient requires that it include means for limiting the current that can flow under any condition between guard and true ground to a value that can flow through the patient without harm.

Whereas the invention will be described in connection with an electrocardiographic system, it will be understood that it could be used in any system deriving electrical signals from electrodes applied to the body, such as electroencephalography and electromyography.

THE DRAWINGS

Figure 1:
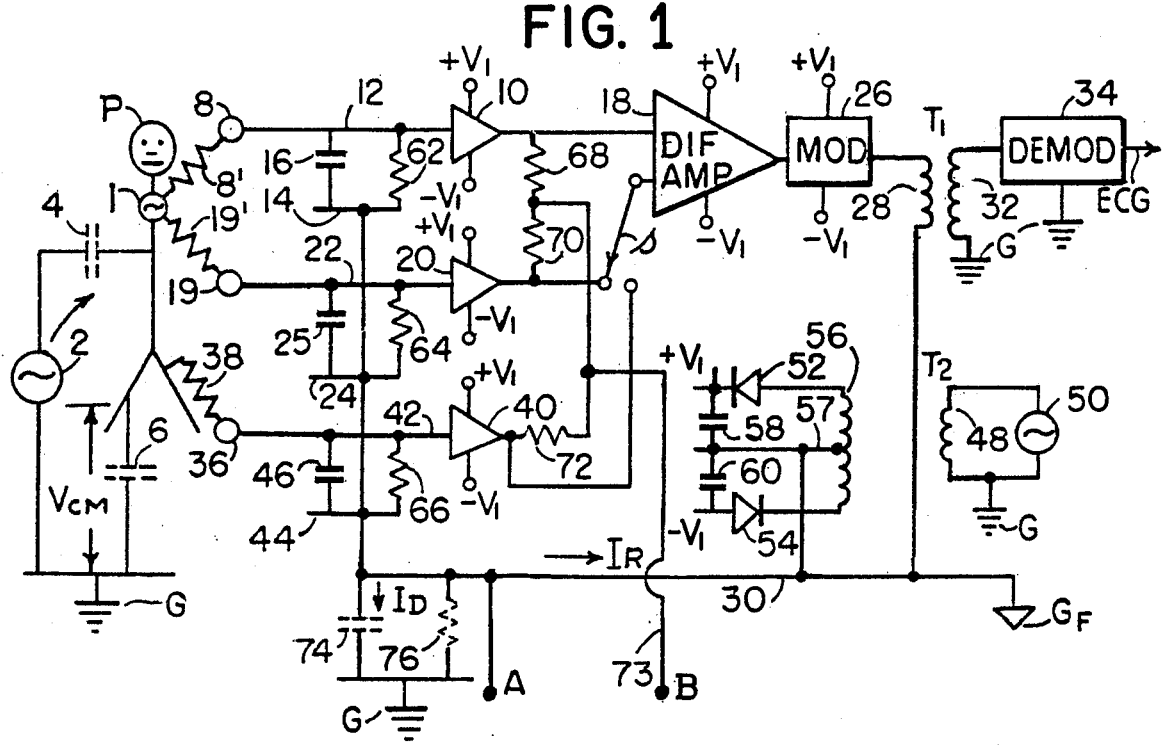
FIG. 1 is a schematic diagram of an electrocardiograph system.

FIG. 1 illustrates the general type of circuit used for deriving a signal proportional to the voltage difference between a pair of electrodes applied to the patient's body. Stray impedances are shown in dotted lines. Source 1 applies the desired differential ECG signals, and the numeral 2 indicates a source of undesired ambient potentials such as may be introduced by a power cord. The source 2 is shown as being coupled to a patient P via a stray capacitance represented by a capacitor 4. The common mode potential, $V_{CM}$, is at all points on the patient's body and its amplitude relative to the ambient potential depends on the voltage dividing action of the stray capacitance represented by the capacitor 4 and the stray capacitance between the patient and true ground that is represented by a capacitor 6. The impedance between a right arm electrode 8 and the patient's body is represented by a resistor 8'. The electrode 8 is connected to an input of a unity gain buffer amplifier 10 via a lead 12 and the distributed capacitance between the lead 12 and its shield 14 is represented by a capacitor 16. The output of the amplifier 10 is connected to an input of a difference amplifier 18. Similarly, a left arm electrode 19 having an impedance between it and the patient's body represented by a resistor 19' is connected to an input of a unity gain buffer amplifier 20 via a lead 22. The distributed capacitance between the lead 22 and its shield 24 is represented by a capacitor 25. The output of the amplifier 20 is connected via one terminal of a switch s to the other input of the difference amplifier 18. Although the coupling of the buffer amplifiers to the difference amplifier 18 may include a Wilson network, this is not shown in order to simplify the drawing.

The output of the difference amplifier 18 is coupled to a modulator 26 that may be one of many types. A primary winding 28 of a transformer $T_1$ is connected between the output of the modulator 26 and a guard bus 30 that is connected to a floating ground or guard indicated at $G_F$. The secondary winding 32 of the transformer $T_1$ is connected between true ground, G, and a demodulator 34 which derives the ECG signal at its output.

If other electrodes are used, as in a selectable lead or multivector system, they would be coupled to the difference amplifier 18 in a manner similar to the way in which the electrodes 8 and 19 are coupled, e.g., an electrode 36 having an impedance between it and the patient's body represented by a resistor 38 is connected to the input of a buffer amplifier 40 via a lead 42. The distributed capacitance between the lead 42 and its shield 44 is represented by a capacitor 46. The output of the amplifier 40 is connected to another terminal of the switch s. In the position shown, the switch s conducts the signal at the output of the buffer amplifier 20 to the difference amplifier 18, but with the switch s in its other position, it conducts the signal at the output of the buffer amplifier 40 to the difference amplifier 18.

The circuits directly coupled to the patient are referenced to a floating ground or guard by supplying them with operating potentials, $+V_1$ and $-V_1$, that are positive and negative with respect to the guard $G_F$. These potentials are applied to the buffer amplifiers 10, 20 and 40, the difference amplifier 18, and the modulator 26. The power supply is comprised of a transformer $T_2$ having a primary winding 48 connected at one end to true ground G and in shunt with a source of alternating current voltage 50. Oppositely poled diodes 52 and 54 are respectively connected between the ends of a secondary winding 56 of the transformer $T_2$ and its center tap 57 via capacitors 58 and 60. The guard bus 30 is connected to the center tap 57 and to the shields 14, 24 and 44. It will be understood by those skilled in the art that whereas separate transformers $T_1$ and $T_2$ are respectively used for coupling signals and providing power, techniques exist for performing both of these functions with a single transformer; but however this is accomplished, the circuits directly connected to the patient P and the primary winding 28 of the transformer $T_1$ are to be referenced to floating ground or guard $G_F$.

THE PROBLEM

The patient's body and the floating ground $G_F$, which is the point to which the inputs of the buffer amplifiers 10 and 20 are referred, are a first set of diagonally opposed points of a bridge circuit, and the electrodes 8 and 19 are a second set. One pair of arms of the bridge is formed by the impedances 8' and 19' between the patient's body and the electrodes 8 and 19, and the other pair of arms is formed by the distributed capacitances 16 and 25. The input impedances of the amplifiers 10 and 20 are so large as to have little effect on the bridge circuit even though they are part of it. Whereas the impedances of the distributed capacitances 16 and 25 can be made very nearly equal, the impedances 8' and 19' are very seldom equal because they depend on the variable factors involved in the application of the electrodes 8 and 19 to the patient's body. Inasmuch as the source 1 of ECG potentials is connected in series with the arms of the bridge, imbalance in the bridge, per se, has no effect on the form of the ECG voltages derived to the buffer amplifiers 10 and 20, but because a substantial fraction of the common mode potential $V_{CM}$ is connected between the first set of diagonal points of the bridge, namely, the patient's body and the floating ground $G_F$, any imbalance will cause unequal fractions of the common mode potential to appear at the electrodes 8 and 19 which are the second set of diagonal points of the bridge. This converts the common mode interference voltage to a differential signal applied to the buffer amplifiers 10 and 20. Because the common mode potential $V_{CM}$ is much larger than the ECG potentials, even a small imbalance in the bridge can cause a differential interference signal at the input of the difference amplifier 18 that is larger than the desired differential ECG voltages.

THE SOLUTION

The circuit described below drives the floating around $G_F$ toward $V_{CM}$ so that the fraction of the common mode voltage which excites the bridge circuit is greatly reduced. Therefore, regardless of the degree of imbalance in the bridge, smaller interference signals appear at the electrodes 8 and 19. If the voltage on $G_F$ is made equal to $V_{CM}$, the bridge excitation and the resulting interference becomes zero.

Figure 1A:
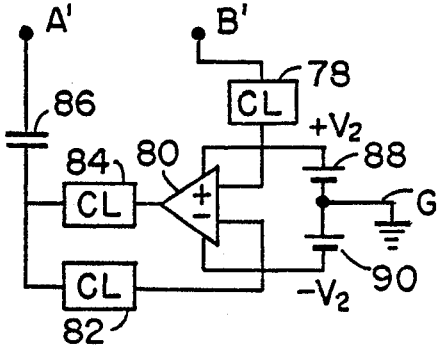
FIGS. 1A and 1B are schematic diagrams of circuits incorporating the invention that are coupled to the circuit of FIG. 1 at points A and B.
Figure 1B:
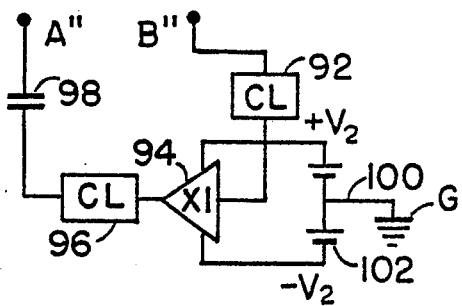

The following components of FIG. 1 are used with the embodiments of the invention illustrated in FIGS. 1A and 1B. Bias current resistors 62, 64 and 66 are respectively connected between the inputs of the buffer amplifiers 10, 20 and 40 and the bus 30. For convenience of reference, a terminal A is connected to the bus 30. Resistors 68, 70 and 72 of equal value are respectively connected between the outputs of the buffer amplifiers 10, 20 and 40 and a terminal B so that the voltage $V_{CM}$ appears at the point B. Since the output impedance of the buffer amplifiers is low, the resistors 68, 70 and 72 have negligible loading effect and do not affect the form or magnitude of the ECG signal. A dotted capacitor 74 and a dotted resistor 76 that are shown in parallel between the bus 30 and true ground represent the distributed impedance between the guard $G_F$ and true ground.

Reference is now made to the circuit of FIG. 1A that is to be connected to the circuit of FIG. 1 by respectively connecting its points A' and B' to the points A and B of FIG. 1. Current limiters are used to protect the patient, but because of their typically high impedance, special circuit configurations have to be used. A current limiter 78 is connected between the points B and the non-inverting input of an operational amplifier 80. Current limiters 82 and 84 are connected in series between the inverting input and the output of the operational amplifier 80, and a capacitor 86 is connected between the junction of the current limiters 82 and 84 and the point A. A power supply, herein schematically illustrated as being comprised of batteries 88 and 90 having opposite terminals connected to true ground G, supplies the positive and negative operating potentials $+V_2$ and $-V_2$ for the operational amplifier 80 so that it is therefore referenced to true ground G. The operational amplifier 80 in conjunction with the current limiters 78, 82 and 84 operates as a unity gain amplifier. The amplifier 80 is controlled by the common mode potential $V_{CM}$ at point B and drives the bus 30 so as to make the impedance at the inputs of the buffer amplifiers 10 and 20 very high for common mode potentials. Inasmuch as the operational amplifier 80 is directly connected to true ground G without any intervening impedance, the current limiters 78, 82 and 84 are provided for the safety of the patient.

OPERATION

As previously stated, the patient P and the floating ground, $G_F$, are a first set of diagonal points in the bridge. The common mode potential $V_{CM}$ at the junction of the resistors 68 and 70 is applied via the points B and B' and the current limiter 78 to the non-inverting input of the amplifier 80. If the gain of the amplifier 80 and its associated circuit is K, its output, which is coupled by the capacitor 86 to the floating guard 30 via the points A and A', is $KV_{CM}$. The common mode current, $I_{CM}$, flowing between the patient P and the floating ground $G_F$, or between the first set of diagonal points of the bridge, may be expressed as $$I_{CM} = \frac{V_{CM} - KV_{CM}}{z} \quad (1)$$

where z is the impedance of the circuit components between the diagonal points. The effective impedance Z between these points may be expressed as $$Z = \frac{V_{CM}}{I_{CM}} = V_{CM} \cdot \frac{z}{V_{CM}(1-K)} = \frac{z}{1-K} \quad (2)$$

Therefore, as K approaches unity, the effective impedance Z approaches infinity and the common mode current $I_{CM}$ reduces to zero. Accordingly, the differential interference voltage produced by $V_{CM}$ at the second set of diagonal points, i.e., at the electrodes 8 and 19, also reduces to zero. If K is not unity, the current $I_{CM}$ will not be zero and will be divided between the upper and lower branches of the bridge so that any imbalance will cause different fractions of $V_{CM}$ to appear at electrodes 8 and 19 and cause interference in the final display. The term "unity gain amplifier" as used herein includes an amplifier that provides unity gain or nearly unity gain between points B and A in the circuits.

The amplifier 80 is a current supply means that is coupled between true ground, G, and floating ground, $G_F$, so as to conduct current therebetween under the control of the common mode voltage, $V_{CM}$, on the floating circuit at the junction of the resistors 68 and 70. The stray impedances 74 and 76 provide a return path from floating ground to true ground and the value and direction of flow of the current through the stray impedances can be such as to make the common mode potential of the floating ground bus 30 equal to the common mode potential of the points B and B'.

The purpose of the capacitor 86 is to prevent D.C. latchup. This does not interfere with the operation of the circuit described because the common mode potential $V_{CM}$ is always A.C.

Another embodiment of the invention is illustrated in FIG. 1B wherein the points A" and B" of the circuit are respectively connected to the points A and B of FIG. 1. A current limiter 92 is connected between the point B" and the input of a unity gain buffer amplifier 94, and a current limiter 96 and a capacitor 98 are connected in series between the output of the amplifier 94 and the point A". A power supply schematically represented by batteries 100 and 102 having opposite poles connected to true ground G provides positive and negative operating potentials $+V_2$ and $-V_2$ to the amplifier 94 so that it is referenced to true ground G. The amplifier 94 and the associated circuit acts as a unity gain amplifier driving the bus 30, or guard $G_F$, so as to make the impedance at the inputs of the buffer amplifiers 10 and 20 or 40 very high for common mode potentials. Inasmuch as the amplifier 94 is directly connected to true ground G without any intervening impedance, current limiters 92 and 96 are provided for the safety of the patient.

In the embodiment of FIG. 1B, the buffer amplifier 94 operates as a current supply means connected between true ground G and floating ground $G_F$ so as to conduct current therebetween under control of voltage on the floating circuit.

The circuit of FIG. 1B operates in a manner similar to that of FIG. 1A to increase the impedance to common mode currents between the patient's body and the floating group $G_F$.

It will be apparent to those skilled in the art that the resistors 68, 70 and 72 coupling the common mode potential on the floating circuits to the point B could be connected to the inputs of the buffer amplifiers 10, 20 and 40 respectively and that in either case only one of the resistors need to be used. It would also be possible to use only one buffer amplifier, in which case the direct connection replacing the other buffer amplifier would be the guard. Other circuits embodying the principles of the invention are described in U.S. Patent Applications having the same title as this application and filed concurrently herewith in the names of Dr. Arthur Miller and Richard H. McMorrow, Jr.

Under conditions where there is no danger of injurious current flowing through the patient, the current limiters may be shorted out.

I claim:

1. A circuit for coupling the difference between potentials supplied by two electrodes in contact with the body of a patient and conducted by shielded leads to the inputs thereof to an output referenced to ground in such manner as to minimize the effect of any common mode voltage and provide a high impedance between the patient and ground without requiring the attachment of another electrode to the patient, comprising a point of ground potential,
   a point of floating ground potential,
   two input terminals to which electrode leads may be respectively attached,
   a differential amplifier circuit having two inputs and an output, said inputs respectively coupled to said input terminals,
   a power supply coupled to provide operating potentials for said differential amplifier circuit, said power supply being referenced to said point of floating ground potential,
   output terminals, one of which is connected to said point of ground potential,
   means coupling the differential amplifier signals at the output of said differential amplifier to said output terminals, said coupling means maintaining a high impedance to ground for the common mode signals at the output of said differential amplifier,
   a terminal to which shields of electrode leads may be attached, said terminal being connected to said point of floating ground potential, and
   a unity gain amplifying circuit means referenced to ground, said unity gain amplifying circuit means having an input connected by means exclusive of the body of a patient to a point in said differential amplifier circuit at which common mode voltages may appear and an output connected to said point of floating ground potential, the said unity gain amplifying circuit means having means for limiting current flowing between ground and both its input and its output, said latter means limiting the current that can flow to a value that is low enough to protect the patient from electrical shock.

2. A circuit as set forth in claim 1 wherein said means for limiting current that can flow between ground and the input and output of the unity gain amplifying circuit means is comprised of a first current limiting means connected between the input of said unity gain amplifying circuit means and the point in said differential amplifier circuit to which the input is coupled and a second current limiting means connected between the output of said unity gain amplifying circuit means and said point of floating ground potential.

3. A circuit as set forth in claim 1 or 2 having a buffer connected between at least one of said input terminals and an input of said differential amplifier circuit and wherein the input of said unity gain amplifying means is connected to said at least one of the inputs of said differential amplifier circuit.

4. A circuit as set forth in claim 1 wherein said unity gain amplifying circuit means is comprised of an operational amplifier having a non-inverting input, an inverting input and an output and wherein
   a first current limiter is connected between said non-inverting input and an input of said differential amplifier circuit,
   second and third current limiters are connected in series between the output of said operational amplifier and its inverting input,
   means are provided for coupling the junction of said second and third current limiters to said point of floating ground potential, and
   power supply means is provided that is referenced to said point of ground potential, said power supply means supplying operating potentials for said operational amplifier.

5. A circuit as set forth in claim 4 wherein at least one buffer amplifier is connected between one of said input terminals and one of the inputs of said differential amplifier circuit.

6. A circuit for coupling the difference between potentials supplied by two electrodes in contact with the body of a patient and conducted by shielded leads to the inputs thereof to an output referenced to ground in such manner as to minimize the effect of any common mode voltage and provide a high impedance between the patient and ground without requiring the attachment of another electrode to the patient, comprising
   a point of floating ground potential,
   a point of ground potential, there being an unavoidable stray impedance between said point of floating ground potential and said point of ground potential,
   a differential amplifier having two inputs and an output, said differential amplifier being referenced to said point of floating ground potential,
   means respectively coupling the inputs of said differential amplifier to said input terminals,
   means coupling the output of said differential amplifier to said output terminals, one of said output terminals being connected to said point of ground potential,
   an amplifier circuit referenced to said point of ground potential, said circuit having an input coupled to at least one of said input terminals by an all-hardware circuit and an output coupled to said point of floating ground potential for causing current to pass through said predetermined stray impedance so as to cause said point of floating ground potential to have the same potential as said one input terminal, said amplifier circuit providing sufficient impedance between said input terminal and ground and between its output and ground to protect a patient electrically coupled to said input terminals from electrical shock, and
   a terminal to which the shields of leads connected to said input terminals may be electrically attached, when said leads are present, said latter terminal being connected to said point of floating ground potential.

* * * * *